United States Patent
Agaiby (10) Patent No.: US 9,927,365 B2
(45) Date of Patent: Mar. 27, 2018

(54) GAS ANALYSERS AND A METHOD OF MAKING A GAS ANALYSER

(75) Inventor: Hany Agaiby, Warwickshire (GB)

(73) Assignee: AG Instruments Ltd., Kenilworth (GB)

( * ) Notice: Subject to any disclaimer, the term of this patent is extended or adjusted under 35 U.S.C. 154(b) by 146 days.

(21) Appl. No.: 14/352,219

(22) PCT Filed: Oct. 21, 2011

(86) PCT No.: PCT/GB2011/052051
§ 371 (c)(1),
(2), (4) Date: Apr. 16, 2014

(87) PCT Pub. No.: WO2013/057460
PCT Pub. Date: Apr. 25, 2013

(65) Prior Publication Data
US 2014/0264027 A1    Sep. 18, 2014

(51) Int. Cl.
*G01N 21/84*      (2006.01)
*G01N 21/3504*   (2014.01)
*G01N 33/00*      (2006.01)

(52) U.S. Cl.
CPC ......... *G01N 21/84* (2013.01); *G01N 21/3504* (2013.01); *G01N 33/0032* (2013.01); *G01N 33/0009* (2013.01); *G01N 2201/0221* (2013.01); *Y10T 29/49002* (2015.01)

(58) Field of Classification Search
CPC .................................. G01J 5/10; G01N 21/359
See application file for complete search history.

(56) References Cited

U.S. PATENT DOCUMENTS

| | | | |
|---|---|---|---|
| 4,323,777 A | | 4/1982 | Baskins et al. |
| 4,670,405 A | * | 6/1987 | Stetter .................... G01N 30/78 422/98 |
| 5,060,508 A | * | 10/1991 | Wong ..................... G08B 29/20 356/437 |
| 7,336,191 B2 | * | 2/2008 | Drews .................. G01N 33/004 340/632 |
| 2002/0152037 A1 | * | 10/2002 | Sunshine ................ C02F 1/008 702/22 |
| 2005/0126264 A1 | * | 6/2005 | Komninos .............. G01M 3/24 73/40.5 A |

(Continued)

FOREIGN PATENT DOCUMENTS

| | | |
|---|---|---|
| CA | 2395563 A1 | 2/2004 |
| WO | WO0194915 A1 | 12/2001 |

OTHER PUBLICATIONS

PCT/GB2011/052051, International Search Report, dated May 31, 2012, European Patent Office, P.B. 5818 Patentlaan 2 NL—2280 HV Rijswijk.

*Primary Examiner* — Christine Sung
(74) *Attorney, Agent, or Firm* — Pehr B. Jansson; The Jansson Firm (57) ABSTRACT

A method of making a measuring instrument, such as a gas analyser (20), comprises the steps of: selecting one or more measuring devices, such as an electrochemical cell (9) and/or an infrared gas analyser (14), from a group of measuring devices; selecting a tubular profile (5) of the appropriate length for the selected measuring devices; and mounting the selected measuring devices (9, 14) in the tubular profile (5).

27 Claims, 5 Drawing Sheets

(56) References Cited

U.S. PATENT DOCUMENTS

| | | | |
|---|---|---|---|
| 2006/0156789 A1* | 7/2006 | Frank | G01N 33/0006 |
| | | | 73/1.06 |
| 2008/0035848 A1 | 2/2008 | Wong | |
| 2008/0277586 A1* | 11/2008 | Cardinale | G01M 3/002 |
| | | | 250/339.13 |
| 2009/0054798 A1* | 2/2009 | Varney | A61B 5/083 |
| | | | 600/532 |
| 2010/0158758 A1* | 6/2010 | Gustin | F01N 13/008 |
| | | | 422/83 |
| 2011/0281367 A1* | 11/2011 | Walte | G01N 33/0031 |
| | | | 436/93 |
| 2014/0250975 A1* | 9/2014 | Kane | G01N 1/2205 |
| | | | 73/23.31 |
| 2014/0284222 A1* | 9/2014 | Wanek, Jr. | G01N 33/0065 |
| | | | 205/780.5 |

\* cited by examiner

GAS ANALYSERS AND A METHOD OF MAKING A GAS ANALYSER

BACKGROUND OF THE INVENTION

The invention relates to gas analysers and a method of making gas analysers.

A known measuring instrument is a portable gas analyser which measures infrared absorption in a gas cell. The gas cell of the portable gas analyser is a long tube with an infrared source at one end and an infrared detector at the other. Gas is introduced into the tube and is analysed according to the level of absorption of infrared between the source and detector. The known portable gas analyser is relatively long which makes it awkward to transport, carry and use.

There are several problems with the known portable gas analyser. It is not suitable for detecting all gases or concentrations of gas. The gas cell is too short for measuring low concentrations of gas, and too long for measuring high concentrations of gas, where all of the infrared radiation may be absorbed before reaching the detector.

SUMMARY

According to a first aspect of the invention there is provided a manufacturing method of making a plurality of different gas analysers, the method for each gas analyser manufactured comprising the steps of:

selecting one or more measuring devices from a group of measuring devices;

mounting the selected measuring device or measuring devices in a tubular profile of the appropriate length for the selected measuring device or devices, the tubular profile being of a common cross section for all of the gas analysers manufactured.

In this way, a customised measuring instrument can be manufactured which is adapted for particular measurement circumstances and is no larger, in particular no longer, than it needs to be.

The tubular profile may be of any desired shape of profile, such as a round profile.

The method is preferably a method of making a portable gas analyser. The method enables a portable gas analyser to be manufactured which is no larger than it needs to be, which improves portability.

At least one measuring device selected from the group of measuring devices may be a gas analyser device, preferably an infrared gas analyser device. Preferably, a plurality of the measuring devices of the group are infrared gas analyser devices of different lengths. In this way, one or more infrared gas cells of appropriate length can be selected for incorporation in the gas analyser so that the gas analyser is adapted for the intended use and no longer than it needs to be. Where more than one measuring device which is a gas analyser device is selected, the gas analyser devices are preferably connected in series, for example by tubes, for transfer of gas between the gas analyser devices. Preferably, where at least one measuring device which is a gas analyser device is selected, the measuring instrument also includes a pump to pump gas to the or each gas analyser device.

At least one measuring device selected from the group may be an electrochemical cell and/or a photo ionisation detector (PID). By incorporating measuring devices of different types, different parameters, such as different gases and different concentrations, can be measured by the same gas analyser.

Preferably, the selected measuring device or measuring devices are mounted on a common mounting element and the mounting element is inserted into the tubular profile. The common mounting element may take any suitable form and may comprise a chassis or strip, which may be made of metal.

The gas analyser suitably includes a controller. The controller is conveniently a programmable controller and is preferably a touch screen controller. In this way, the controller can be programmed so that the appropriate number of icons, and no more, are available on screen. Also, the icons and other displayed elements can be tailored to the measuring devices incorporated in the gas analyser. The controller may be separate from the tube but preferably is mounted on the outside of the tube.

According to another aspect of the invention there is provided a gas analyser made by the method according to the first aspect of the invention.

The measuring devices are preferably mounted on a common mounting element which is mounted in the tubular profile. The common mounting element may take any suitable form and may comprise a chassis or strip, which may be made of metal.

The tubular profile may be of any desired cross-sectional shape and may be a round profile.

The gas analyser is preferably a portable gas analyser.

At least one of the measuring devices in the gas analyser is a gas analyser device and may be an infrared gas analyser device. The gas analyser may include two gas analyser devices of different lengths. Preferably, a plurality of different measuring devices are gas analyser devices and in that case, at least two of the gas analyser devices are preferably connected in series, for example by tubes, for transferring gas between the gas analyser devices. Alternatively, at least two of the gas analyser devices may be arranged in parallel. Arrangement of the measuring devices in parallel allows a shorter length of tubular profile to be necessary than if the measuring devices are connected in series. The gas analyser may also include a pump to pump gas to the or each gas analyser device.

At least one of the measuring devices in the gas analyser may be an electrochemical cell and/or a photo ionisation detector (PID).

The gas analyser suitably includes a controller. The controller is conveniently a programmable controller and is preferably a touch screen controller. In this way the display can be customised. The controller may be separate from the tube but preferably is mounted on the outside of the tube.

BRIEF DESCRIPTION OF THE DRAWINGS

Embodiments of the invention will now be described by way of example and with reference to the accompanying drawings.

DETAILED DESCRIPTION

Figure 1:
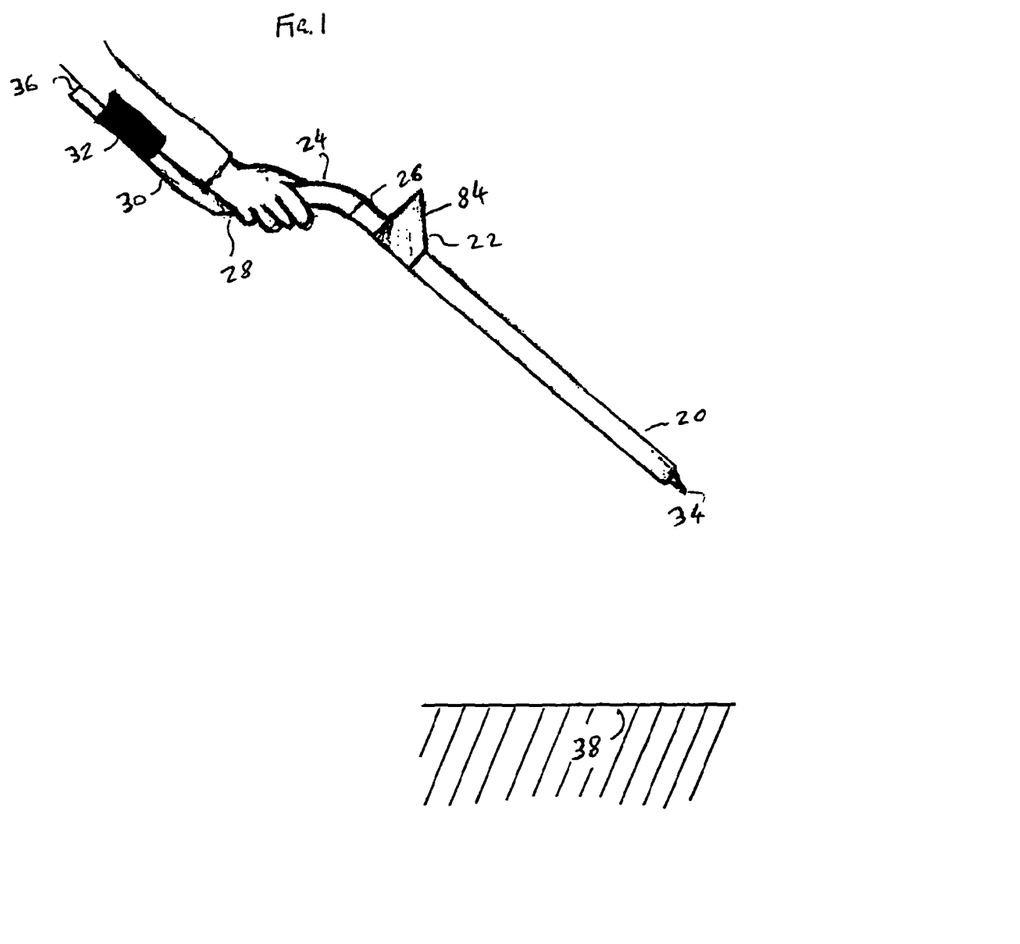
FIG. 1 is a side view of a measuring instrument in a first embodiment of the invention.

The measuring instrument 20 of the embodiment comprises a shell or casing 5 in the form of a tubular profile of round cross section. A display 22 is mounted at the upper end of the measuring instrument 20. A handle 24 is attached to the end 26 of the measuring instrument 20. The handle 24 is generally S-shaped, the middle part 28 of the S being arranged to be grasped by a user, and the portion 30 at the opposite end from the connection to the measuring instrument 20 carrying an arm rest 32 which is curved to receive part of the arm of a user, as shown in FIG. 1. A gas inlet nozzle 34 is provided at the lower end of the measuring instrument 20. The gas outlet at the upper end of the measuring instrument 20 feeds into the tubular handle 24 for emission through the open upper end 36 of the handle 24.

Figure 2:
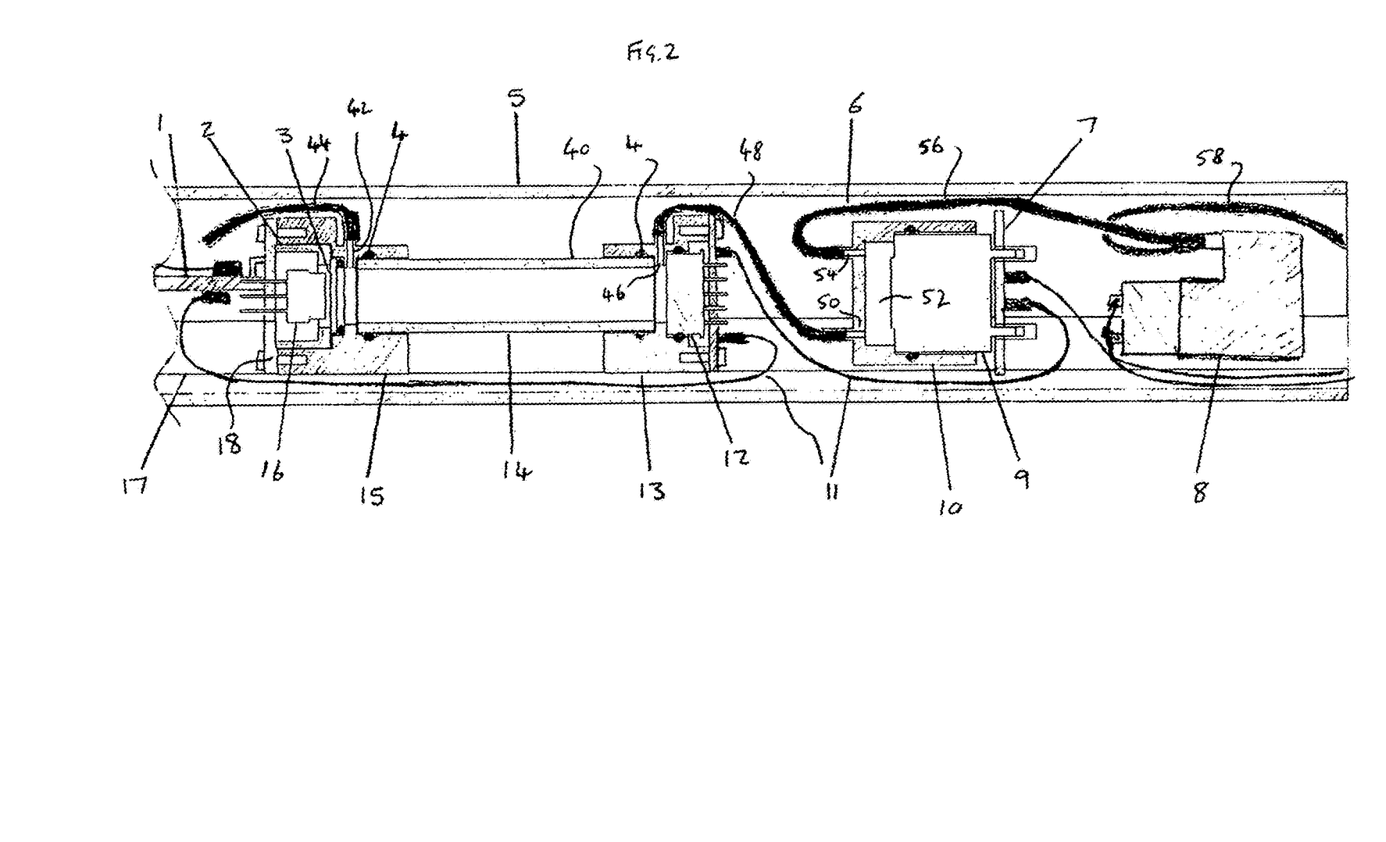
FIG. 2 is a side elevation in cross-section of part of the measuring instrument of FIG. 1.

The measuring instrument 20 of this embodiment is a portable gas analyser. The instrument 20 is particularly suitable for analysis of gases which are heavier than air. A user can stand, comfortably holding the instrument 20 by the handle 24 in the manner shown in FIG. 1, with the gas inlet nozzle 34 near the floor 38. FIG. 2 shows part of the interior of the measuring instrument 20. A mounting strip 17 mounts an infrared gas analyser 40, an electrochemical cell 9 and a pump 8.

The infrared gas analyser 40 comprises a tube 14 with an infrared source 16 at one end and an infrared detector 12 at the other end. A source block 15 mounts the infrared source 16 and the corresponding end of the tube 14. A detector block 13 mounts the infrared detector and the corresponding end of the tube 14. The source block 15 mounts an optical window 3 between the infrared source 16 and the end of the tube 14. The ends of the tube 14 are supported in 0 rings 4 carried by the source and detector blocks 13, 15. The source block 15 defines an aperture 42 which opens between the end of the tube 14 and the optical window 3 to allow gas out of the infrared cell 40. The aperture 42 leads to a hollow projection which is received in the end of a tube 44, the other end of which is at the gas outlet.

Another aperture 46 is provided in the detector block 13 between the detector 12 and the end of the tube 14. The aperture 46 leads to a hollow projection which is received in the end of a gas tube 48.

The other end of the gas tube 48 is received on a hollow projection at the rear of a manifold 10 of the electrochemical cell 9. The hollow projection leads through a bore 50 into a cavity 52 between the manifold 10 and electrochemical cell 9. A further bore 54 leads out of the cavity 52 through the manifold 10 to a further hollow projection defined on the rear of the manifold 10 which receives the end of a further gas tube 56, the other end of which is connected to the pump 8. A further gas tube 58 leads from the pump 8 to the gas inlet 34 of the measuring instrument 20.

Cables 11 carry system bus signals, power and other signals and are connected to the pump 8, electrochemical cell 9 and infrared sensor 12 in series, together with a PCB 1 which is connected to the infrared source 16.

Figure 3:
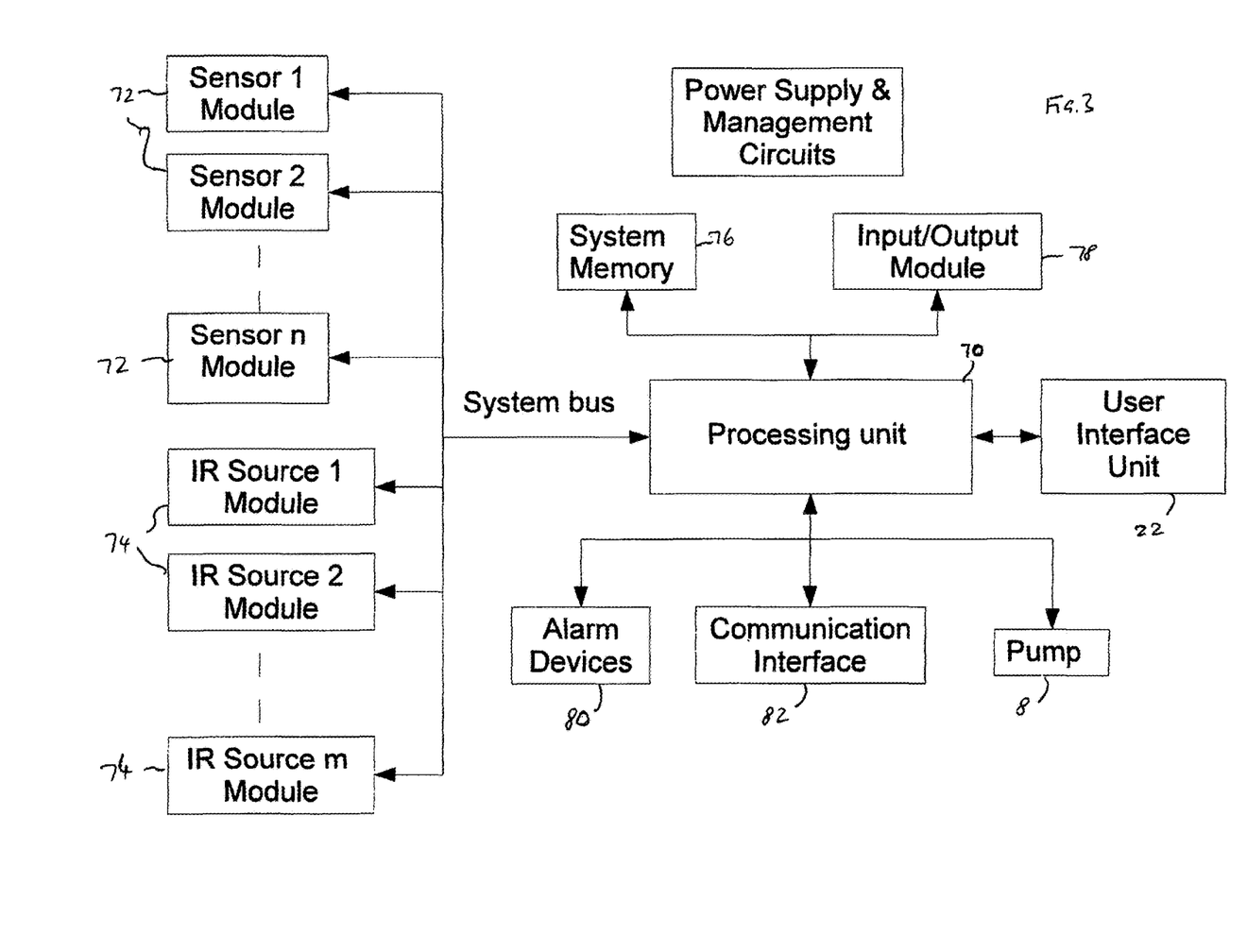
FIG. 3 is a block diagram of the control circuit of the measuring instrument of FIG. 1.

FIG. 3 shows the power supply and management circuits. A processing unit 70 is connected through a system bus to one or more sensor modules 72 and infrared source modules 74, the electrochemical cell 9 being an example of a sensor module 72, and the infrared cell 40 being an example of an infrared module 74. The processing unit 70 is also connected to a system memory 76 and an input/output module 78. The processing unit 70 is also connected to the pump 8, alarm devices 80 and a communication interface 82. The processing unit 70 is also connected to a user interface unit including the display 22.

The display 22 is mounted in a housing 84 which also houses the battery (not shown) which powers the instrument 20.

Figure 4:
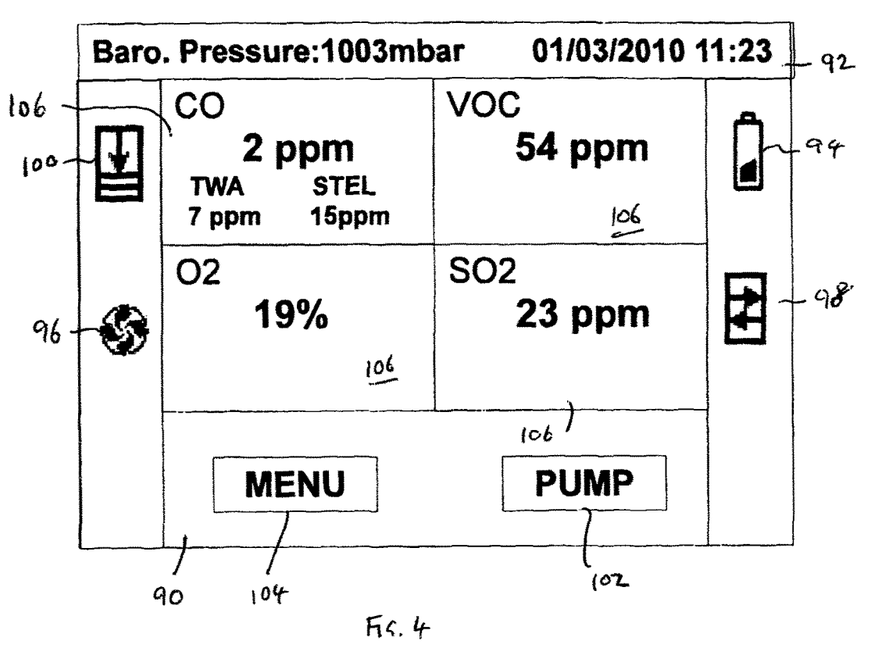
FIG. 4 is a screenshot of the display of the instrument of FIG. 1.

FIG. 4 is an example of a screenshot from the display 22. The display 22 is a touch screen unit. On the screenshot 90 there is a bar 92 across the top to display the barometric pressure, the date and time. At the sides are icons 94, 96, 98, 100 which indicate the status of the instrument 20, for example the battery level 94 and whether the fan is operating, 96. At the bottom of the screen 90 are two buttons, one 102 to control the operation of the pump, and the other 104 to change the menu on the screenshot 90. The central area is divided into four quadrants 106, each quadrant displaying the detected concentration of a different gas.

To make the measuring instrument 20, the user or customer, specifies which gases the instrument 20 is to be used to analyse. Measuring devices are then selected from a group of possible devices. The group can include a photo ionisation detector (PID) and an electrochemical cell 9 and there will also be a selection of gas cell tubes 40 of different lengths to be fitted into infrared detector blocks 13 and source blocks 15 to create infrared gas analysers of different lengths. A plurality of detector blocks 13 and source blocks 15 are provided so that a plurality of infrared gas analysers 40 can be used in a single portable measuring instrument 20. In the present case, a single infrared gas analyser 40 is to be included, and so a single detector block 13 and a single source block 15 are selected together with a gas cell tube 14 of the appropriate length. An electrochemical cell 9 is also selected. A mounting strip 17 is then selected. There may be a plurality of mounting strips 17 of different lengths, so that appropriate length can be selected, or the strip can be simply cut to the appropriate length to mount the selected measuring devices. Thus, the detector block 13 and source block 15 are mounted to the strip 17 with the gas cell tube 14 between them. The electrochemical cell 9 is then mounted on the mounting strip 17 adjacent the infrared gas analyser 40 and the pump 8 is mounted on the mounting strip 17 alongside the electrochemical cell 9. The gas tubes 44, 48, 56, 58 are then connected between the measuring devices, the pump 8 and the inlet nozzle 34 and outlet 36. The cables 11 are also then connected to the devices. A cylindrical profile 5 is then selected which is no longer than it needs to be to receive and encase the strip 17 and the devices thereon. Again, this may be selected from a group of tubes of different lengths, or may simply be cut to the appropriate length. The nozzle 34 is fitted on to the end of the profile 5 and the handle 24 is fitted to the other end. An aperture is cut in the profile 5 through which the cable 11 is passed to be connected to the battery and processing unit 70 which are mounted within the casing 84 of the display 22 which is subsequently mounted on to the outside of the profile 5. Taking into account the selected measuring devices, namely in this case, the electrochemical cell 9 and infrared gas analyser 14, the processing unit 70 is programmed to display appropriate readings on the display screen 22.

Thus, for example, if a measuring instrument were constructed without a pump, the pump button 102 and pump icon 96 representing the status of the pump could both be omitted. Equally, while the screenshot 90 shows readings for carbon monoxide, oxygen, sulphur dioxide and volatile organic compounds, the concentrations of other gases could be detected and displayed, and the screen 22 may be divided into more or fewer than four regions, if more than four or less than four gases are to be analysed.

In use, the user grasps the handle 24 at the middle section 28 of the S-shape so that their forearm is received in the armrest 32. The nozzle 34 at the end of the measuring instrument 20 can then be pointed downwards towards the floor 38 so that gas from that region can be drawn by the pump 8 through the nozzle 34 and through the tubes 58, 56, 48 to the electrochemical cell 9 and infrared gas analyser 40 for analysis, and then through the tube 44 to the gas outlet 36. The results of analysis by the electrochemical cell 9 and infrared gas analyser 14 are fed back to the processing unit 70 through the bus lines 11 to be displayed on the display 22.

Thus, it can be seen that, from a group of measuring devices, an appropriate selection can be made in view of the user's requirements in order to construct a portable measuring instrument which is customised to the user's requirements. By using a standard mounting method, assembly is standardised. As both the strip 17 and profile 5 can be selected in different lengths or cut to length, the instrument 20 can be made no longer than it needs to be. The controller, in the form of the touch screen display 22 and programmable processing unit 70, is also customisable so that only the readouts, buttons and icons required are displayed. Thus, an efficient and compact instrument can be made using an intelligent, customisable manufacturing process.

In an alternative embodiment, the handle 24 is not fitted, and instead a belt is provided for the user to wear. The belt includes a loop through which the tubular profile 5 can be inserted, the loop being smaller than the diameter of the profile 5 and display casing 84 so that the instrument 20 is suspended from the belt loop to hang by the user's side. The user can look down at the display 22.

Figure 5:
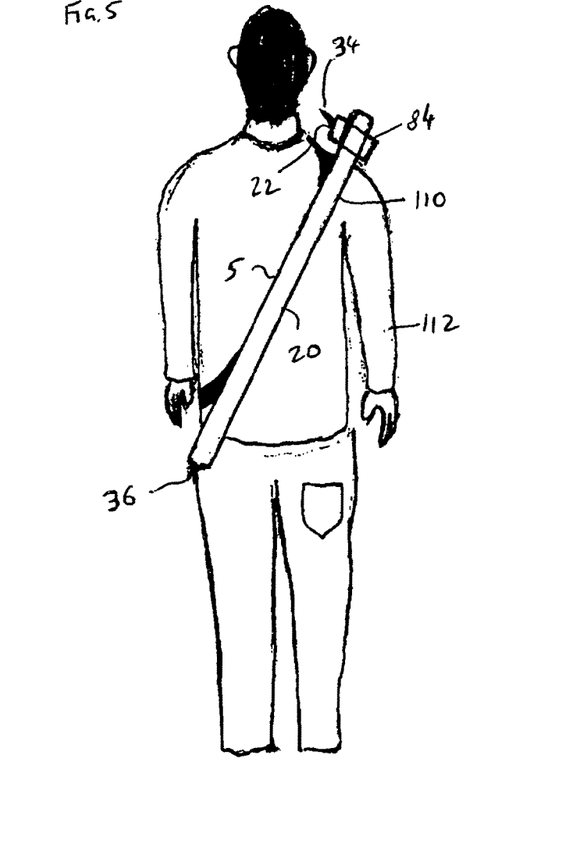
FIG. 5 is a view of a measuring instrument in a second embodiment of the invention.

A further embodiment is shown in FIG. 5. The embodiment is similar to the first embodiment and only the differences from the first embodiment will be described. The same reference numerals will be used for equivalent features.

In this case, the handle 24 of the first embodiment is omitted, and instead a length of webbing 110 is attached to the ends of the profile 5 so that the measuring instrument 20 can be slung over the shoulder of a user 112 in the manner of a rifle, as shown in FIG. 5. The gas inlet 34 in this case is provided on the side of the display casing 84, adjacent the head of the user. The gas outlet 36 is at the opposite end of the profile 5.

This embodiment is suitable for analysing gas at the level of which it will be breathed in by people, namely at nose and mouth level.

The invention claimed is:

1. A manufacturing method of making a plurality of different gas analysers, the method for each gas analyser manufactured comprising the steps of:
    selecting a plurality of gas analyser devices of different types from a group of gas analyser devices, each gas analyser device comprising a gas inlet, a gas outlet, a gas chamber, and a detector, one of the types in the group being an infrared gas analyser device, one of the selected gas analyser devices being an infrared gas analyser device;
    selecting a common mounting element of a length sufficient to accommodate the selected gas analyser devices in-line with respect to one another;
    mounting the selected gas analyser devices on the common mounting element in-line with respect to one another;
    selecting a tubular profile of an appropriate length to accommodate the in-line arranged selected plurality of gas analyser devices, and
    inserting the mounting element into the tubular profile.

2. The method as claimed in claim 1, wherein the profile selecting step comprises
    selecting a round tubular profile of the appropriate length for the selected gas analyser measuring devices.

3. The method as claimed in claim 1 wherein the step of selecting a gas analyser device includes selecting a detector block, selecting a source block, and mounting a gas cell tube of a desired length between them to form the infrared gas analyser device.

4. The method as claimed in claim 1, wherein the device selecting step comprises selecting a plurality of infrared gas analyser devices of different lengths.

5. The method as claimed in claim 1, wherein the method further comprises connecting the gas analyser devices in series for transfer of gas between the gas analyser devices.

6. The method as claimed in claim 1, wherein each of the gas analysers includes a pump to pump gas to the gas analyser devices.

7. The method as claimed in claim 1, wherein the device selecting step includes selecting an electrochemical cell.

8. The method as claimed in claim 1, wherein the device selecting step includes selecting a photo ionisation detector (PID).

9. The method as claimed in claim 1, wherein each of the gas analysers includes a programmable controller.

10. The method as claimed in claim 9, wherein the method includes mounting the controller on the tubular profile.

11. The method as claimed in claim 9, wherein the controller is a touch screen controller.

12. The method as claimed in claim 1, wherein the mounting step includes mounting two gas analyser devices in the tubular profile in parallel.

13. The method as claimed in claim 1, further comprising:
    electrically connecting the plurality of gas analyser devices in series.

14. The method as claimed in claim 1, further comprising the step of:
    cutting the selected common mounting element to an appropriate length.

15. A gas analyser comprising
    a plurality of gas analyser devices of different types selected from a group of gas analyser devices, each gas analyser device comprising a gas inlet, a gas outlet, a gas chamber, and a detector, one of the types in the group being an infrared gas analyser device, one of the selected gas analyser devices being an infrared gas analyser device;
    a common mounting element selected to be of a length sufficient to mount said plurality of gas analyser devices in-line with respect to one another;
    the selected gas analyser devices mounted in-line with respect to one another on the common mounting element; and
    a tubular profile of an appropriate length for entirely housing the selected gas analyser devices internally within said tubular profile.

16. The gas analyser as claimed in claim 15 further comprising a detector block, a source block, and a gas cell tube of a desired length between the detector block and the source block to form the infrared gas analyser device.

17. The gas analyser as claimed in claim 15, wherein the plurality of gas analyser devices comprise a plurality of infrared gas analyser devices of different lengths.

18. The gas analyser as claimed in claim 15, wherein the plurality of gas analyser devices are connected in series for transfer of gas between the gas analyser devices.

19. The gas analyser as claimed in claim 15, wherein the gas analyser further comprises a pump to pump gas to the plurality of gas analyser devices.

20. The gas analyser as claimed in claim 15, wherein the plurality of gas analyser devices comprises an electrochemical cell.

21. The gas analyser as claimed in claim 15, wherein the plurality of gas analyser devices comprises a photo ionisation detector (PID).

22. The gas analyser as claimed in claim 15, wherein the gas analyser further comprises a programmable controller.

23. The gas analyser as claimed in claim 22, wherein the controller is mounted on the tubular profile.

24. The gas analyser as claimed in claim 22, wherein the controller is a touch screen controller.

25. The gas analyser as claimed in claim 15, wherein the plurality of gas analyser devices comprises two gas analyser devices mounted in parallel inside the tubular profile.

26. The gas analyser of claim 15, wherein the plurality of gas analyser devices are connected in a series.

27. A gas analyser made according to a method comprising:

selecting a plurality of gas analyser devices of different types from a group of gas analyser devices, each gas analyser device comprising a gas inlet, a gas outlet, a gas chamber, and a detector, one of the types in the group being an infrared gas analyser device, one of the selected gas analyser devices being an infrared gas analyser device;

selecting a common mounting element of a length sufficient to accommodate the selected gas analyser devices in-line with respect to one another;

mounting the selected gas analyser devices on the common mounting element in-line with respect to one another;

selecting a tubular profile of an appropriate length to accommodate the in-line arranged selected plurality of gas analyser devices, and inserting the mounting element into the tubular profile.

* * * * *